United States Patent [19]
Chen

[11] Patent Number: 5,752,936
[45] Date of Patent: May 19, 1998

[54] SAFETY VACUUM SYRINGE WITH TWO OPPOSITE NEEDLES FOR BLOOD SAMPLING

[76] Inventor: Long-Hsiung Chen, 5F. No. 91-3. Sec. 1, Chung-Cheng Rd., Taipei, Taiwan

[21] Appl. No.: 844,333

[22] Filed: Apr. 18, 1997

[30] Foreign Application Priority Data

Feb. 5, 1997 [TW] Taiwan .................. 86202211

[51] Int. Cl.[6] .................................................. A61M 5/00
[52] U.S. Cl. .......................... 604/110; 604/195; 128/763
[58] Field of Search .............................. 604/187, 198, 604/195, 192, 110, 263; 128/763, 764, 765

[56] References Cited

U.S. PATENT DOCUMENTS

| | | | |
|---|---|---|---|
| 4,838,863 | 6/1989 | Allard et al. ............... | 604/195 X |
| 5,374,250 | 12/1994 | Dixon ....................... | 128/763 X |
| 5,423,758 | 6/1995 | Shaw ........................ | 604/195 X |

*Primary Examiner*—John D. Yasko

*Attorney, Agent, or Firm*—Morton J. Rosenberg; David I. Klein; Jun Y. Lee

[57] ABSTRACT

The present invention relates to a safety vacuum syringe with two opposite needles for blood sampling, which mainly comprises a cylindrical barrel, a bell type sleeve, a needle unit, a cylindrical vacuum container, a snapping member, a needle cap, and a bottom cap. When it is desired to sample blood, the vacuum container is pushed into the barrel through the back end thereof, so that the snapping member will be hooked with the bell type sleeve. After finished of the blood sampling, the vacuum container stored with blood is pulled out of the barrel, and the bell type sleeve with the needle unit will be pulled into the barrel, the needle cap and the bottom cap are then recversely inserted into the barrel for bending the needles to be damaged. Alternately, the needle cap can be extended further to form a tube having a tube opening at top end thereof for accommodating said front needle when said needle cap is revesely inserted into said barrel, and the bottom cap is provided with a recessed part at the bottom surface thereof, when said bottom cap is reversely inserted into said barrel, said back needle can be accommodated within said recessed part.

6 Claims, 9 Drawing Sheets

5,752,936

1

SAFETY VACUUM SYRINGE WITH TWO OPPOSITE NEEDLES FOR BLOOD SAMPLING

FIELD OF THE INVENTION

The present invention relates to a safety vacuum syringe for blood sampling, and more particularly to a syringe with the needles being damaged or enclosed after use to prevent the operator from contamination.

BACKGROUND OF THE INVENTION

As the medical science is progressing, the need for a disposable syringe is becoming more important, and the problems of safety and environmental protection should also be seriously considered. Although there have been some safety syringes avaiable in the market, a safety vacuum syringe with two opposite needles is still not avaiable in the market.

SUMMARY OF THE INVENTION

It is therefore an object of the present invention to provide a safety vacuum syringe with two opposite needles for blood sampling, wherein the two opposite needles can be enclosed inside the barrel of the syringe after use to prevent the operator from contamination.

It is another object of the present invention to provide a safety vacuum syringe with two opposite needles for blood sampling, wherein the two opposite needles can be damaged within the barrel of the syringe after use to prevent from using again.

It is a further object of the present invention to provide a safety vacuum syringe with two opposite needles for blood sampling, wherein a needle cap and a bottom cap can be inserted into the barrel of the syringe to strengthen the barrel and prevent the barrel from breaking, and the syringe can be disposed as a whole unit.

BRIEF DESCRIPTIONS OF THE DRAWINGS

The present invention can be better understood by detailed descriptions of the following drawings, in which.

2

Figure 7:
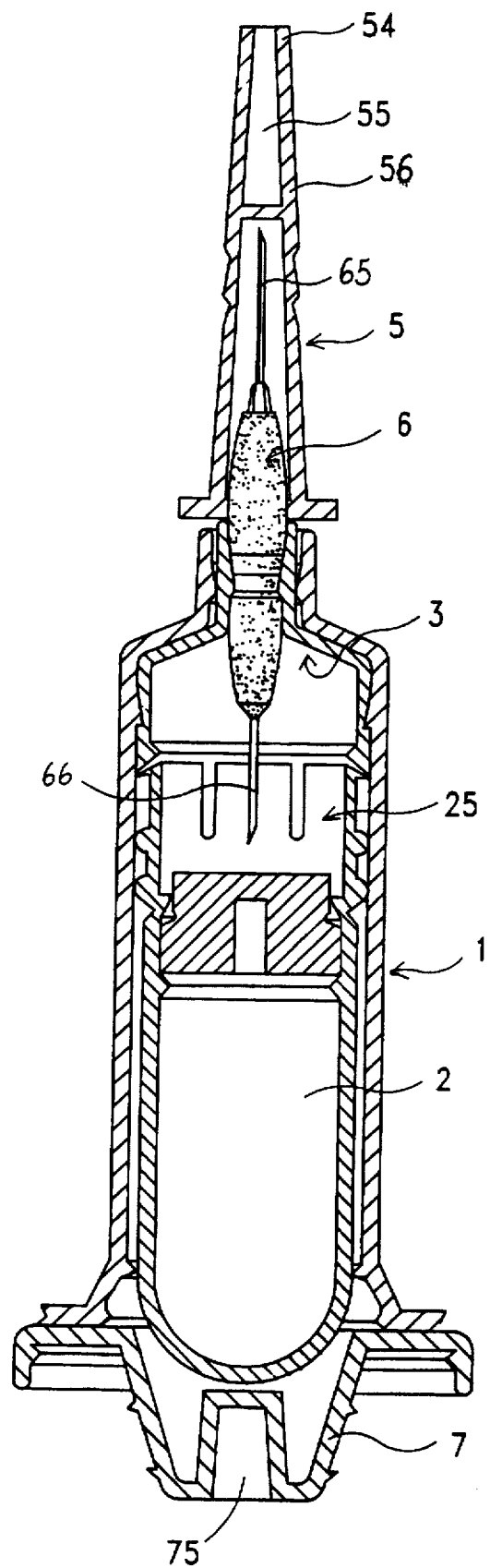
FIG. 7 is a schematic longitudinal sectional view of another embodiment of the present invention before use, which can be used for a syringe with thicker needles.
Figure 8:
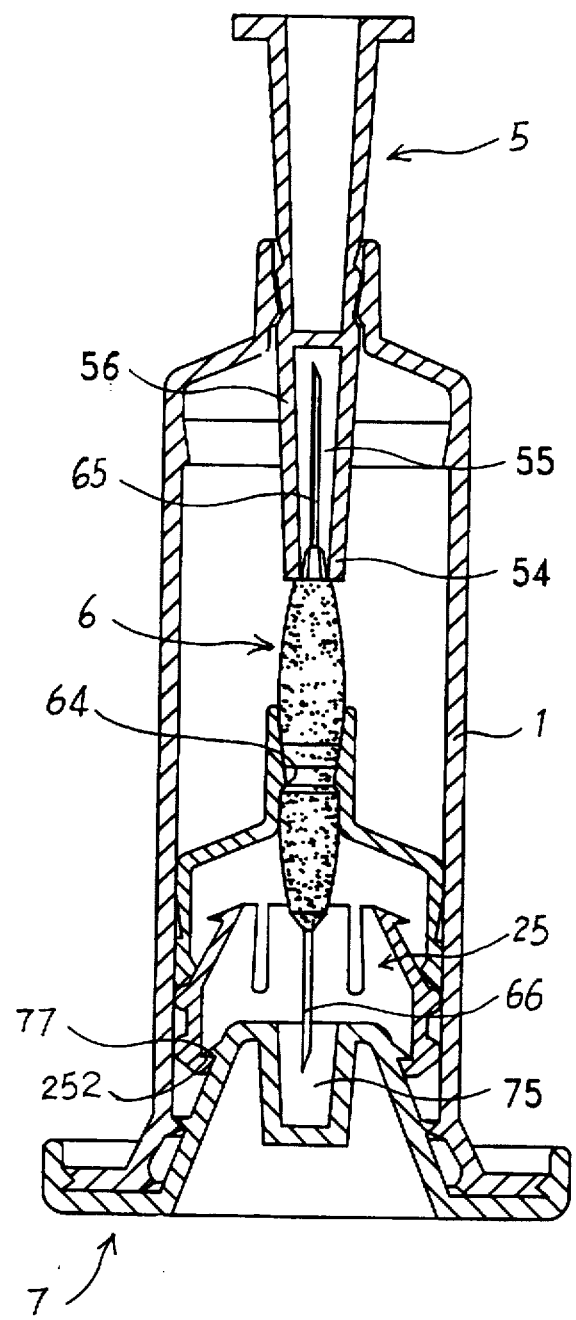

FIG. 8 is a schematic longitudinal sectional view of the preferred embodiment shown in FIG. 7 after blood sampling, wherein the needle cap and the bottom cap are reversely inserted into the barrel of the syringe so that the two opposite needles are enclosed by the two caps.

DETAILED DESCRIPTIONS OF THE INVENTION

Figure 1:
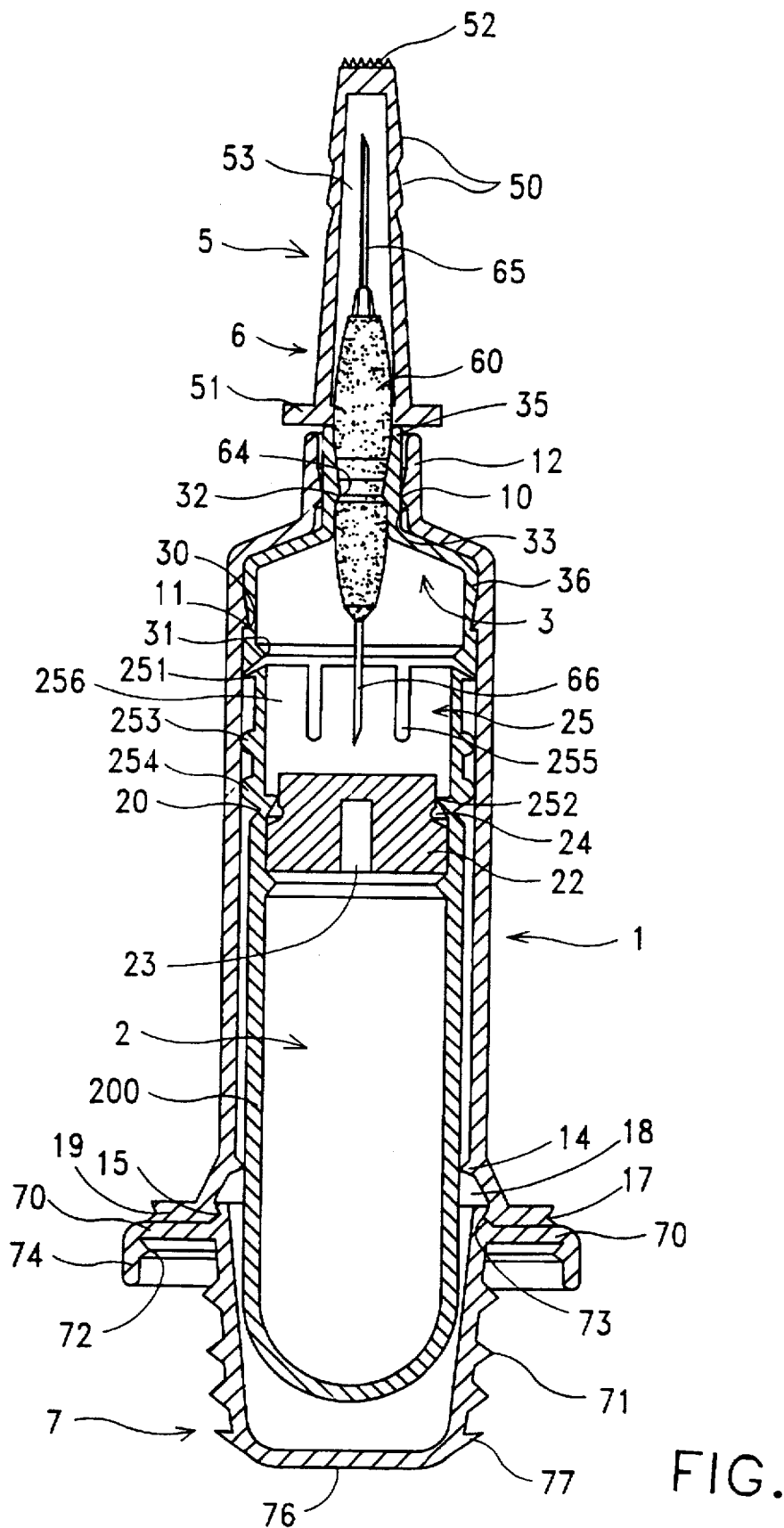
FIG. 1 is a schematic longitudinal sectional view of a preferred embodiment of the present invention before use, which can be used in a syringe with thinner needles.
Figure 1A:
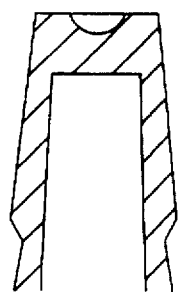
FIG. 1A and 1B are schematic diagrams of the needle cap of other embodiments of the present invention.
Figure 1B:
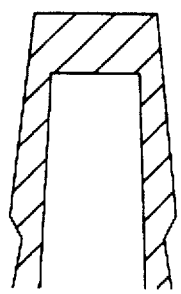
Figure 5:
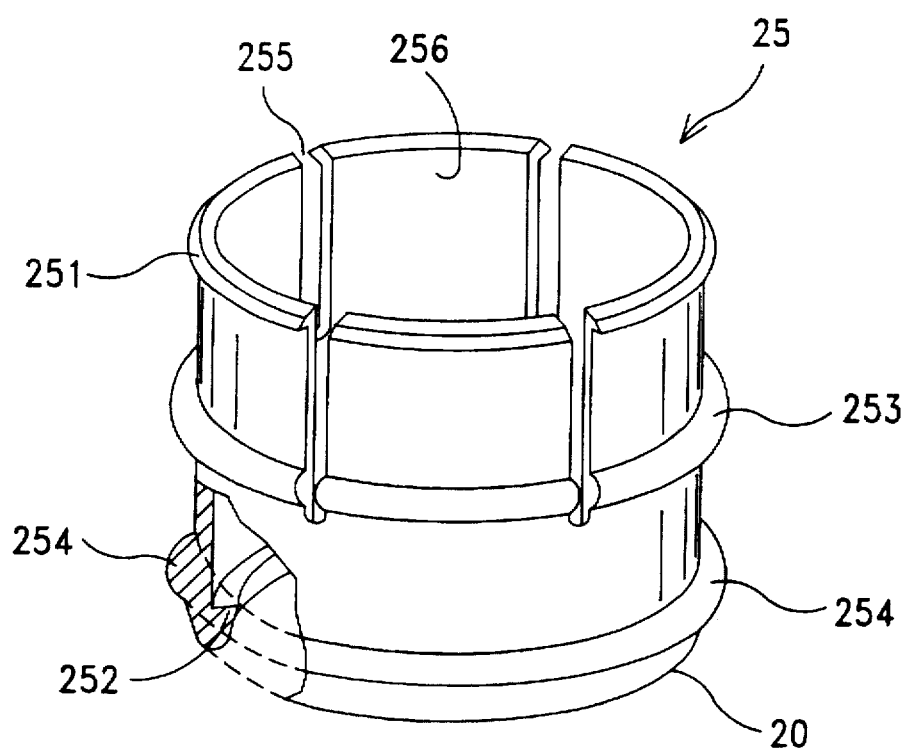
FIG. 5 is a schematic perspective view of a snapping member of the present invention.

Please refer to FIG. 1, which is a schematic longitudinal sectional view of a preferred embodiment of the present invention before use. As shown in the figure, a cylindrical barrel 1 comprises a contracted opening 12 at the front end having a slope annular flange 10 therein, another slope annular flange 11 provided on the inner wall of the barrel 1, a horn opening 18 with a outward flange 19 provided at the back end having annular flange 14 and 15 respectively therein, a groove 17 provided on outer circumference of the flange 19, a bell type sleeve 3 inserted inside the barrel 1 at the front end having a contracted tube 35 and a bell body 36, a slope annular recess 30 provided at outer circumference of the bell body 36 to match with the flange 11 so that the sleeve 3 is held within the bell 1, a slope annular flange 32 provided inside of the contracted tube 35, an annular hook flange 31 provided at the opening of the bell body 36, a needle unit 6 including of a rubber holder 60 and a front needle 65 and a back needle 66 extended through the rubber holder 60, a slope annular recess 64 provided at the waist part of the rubber holder 60 to match with the slope annular flange 32, a cylindrical vacuum container 2 including of a plastic tube 200 for receiving blood and a rubber stopper 22 and a snapping member 25, a blind hole 23 provided in the rubber stopper 22 for being penetrated by the back needle 66, an annular groove 24 provided at the outer waist part of the rubber stopper 22, the snapping member 25 having a fragile annular neck 20 to be connected with the tube 200 and opposite to the annular groove 24, an outward annular hook flange 251 provided at the upper edge of the snapping member 25 (please see FIG. 5), an inward annular hook flange 252 provided at the lower edge of the snapping member 25, two annular flanges 253 and 254 provided at the outer circumference of the snapping member 25, a plurality of longitudinal slots 255 provided at the upper half wall of the snapping member 25 to form a plurality of flexible snapping pieces 256, a needle cap 5 having a front closed end 52 and a back opening flange 51 and tapered from flange 51 toward closed end 52, a plurality of annular hook recesses 50 provided at the outer circumference of the needle cap 5 so that the needle cap 5 can be reversely inserted into the contracted opening 12 and fixed by means of the annular hook recess 50 and the slope annular flange 10 (please see FIG. 6), the top surface of the closed end 52 being formed into a sawtooth shape (FIG. 1), a recessed shape (FIG. 1A) or a plane (FIG. 1B, made of soft plastics), a bottom cap 7 with the bottom surface 76 thereof being formed into one of those shapes of the top surface of the closed end 52 (not shown), an annular flange 70 provide at the opening of the bottom cap 7 and extended downward to form an annular wall 74, an annular flange 72 provided inside of the annular wall 74, an annular recess 73 provided at the top edge of the bottom cap 7 to match with the annular flange 15 of the horn opening 18, a plurality of annular flanges 71 provided at the outer circumference of the bottom cap 7, an annular hook flange 77 provided at the bottom edge of the bottom cap 7.

Figure 2:
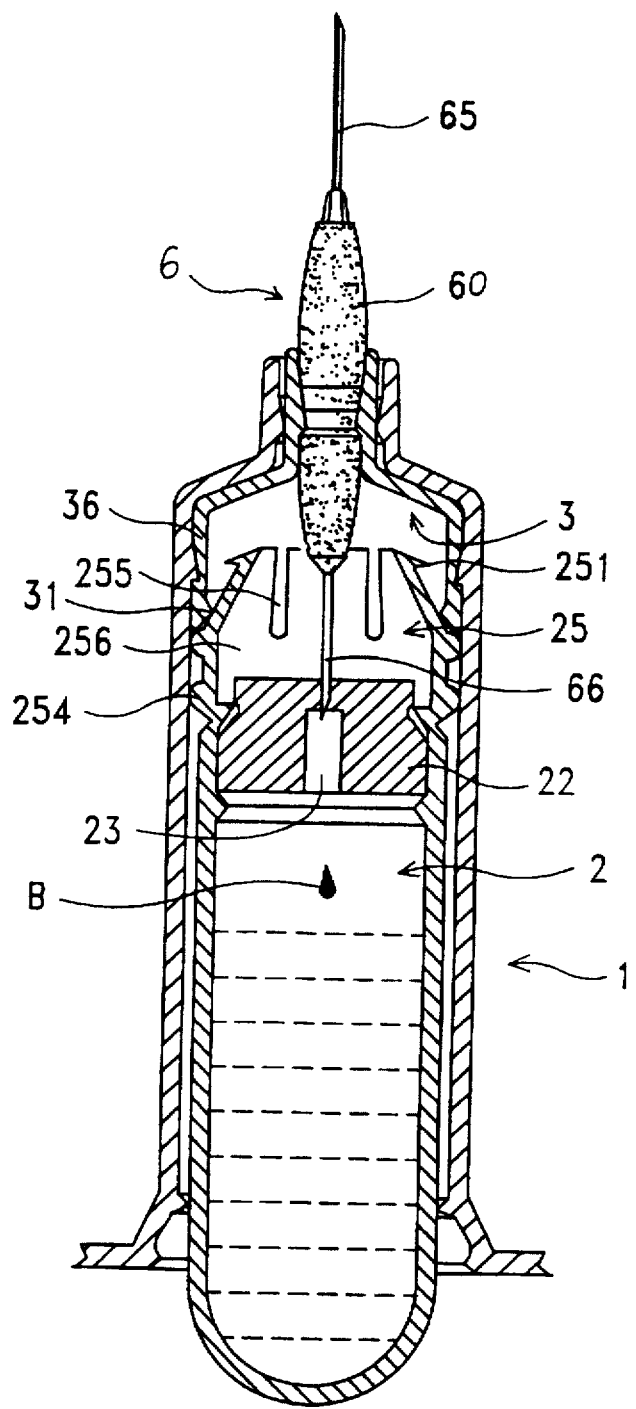
FIG. 2 is a schematic longitudinal sectional view of the preferred embodiment shown in FIG. 1 during using.

Please refer to FIG. 2, which shows that the syringe of the present invention is in use, the needle cap 5 and the bottom cap 7 are removed, and the front needle 65 is pierced into a blood vessel, whereby the vacuum container 2 is pushed forward so that the back needle 66 is pierced into the blind hole 23 of the rubber stopper 22 for blood sampling, while the plurality of flexible snapping pieces 256 at the front end of the snapping member 25 are pushed into the bell body 36.

Figure 3:
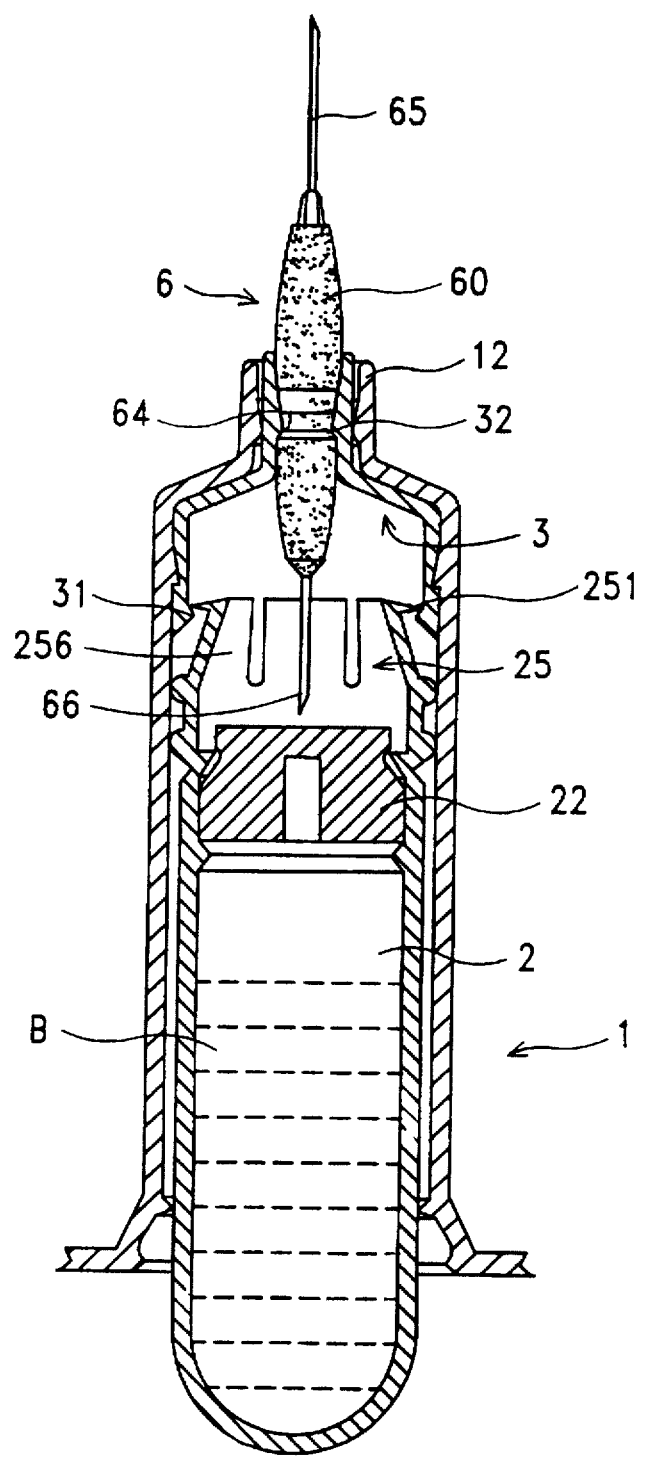
FIG. 3 is a schematic longitudinal sectional view of the preferred embodiment of the present invention after use.

Please refer to FIG. 3, when finished of the blood sampling, the vacuum container 2 stored with blood is pulled backward, the back needle 66 will be released out of the rubber stopper 22 and the front needle 65 will be released out of the human body, while the plurality of flexible snapping pieces 256 of the snapping member 25 gradually expand outward so that the annular hook flange 251 will be hooked with the annular hook flange 31. If continue pulling out of the vacuum container 2, the bell type sleeve 3 will be pulled out of the contracted opening 12 so that the needle unit 6 will be pulled into the barrel 1.

Figure 4:
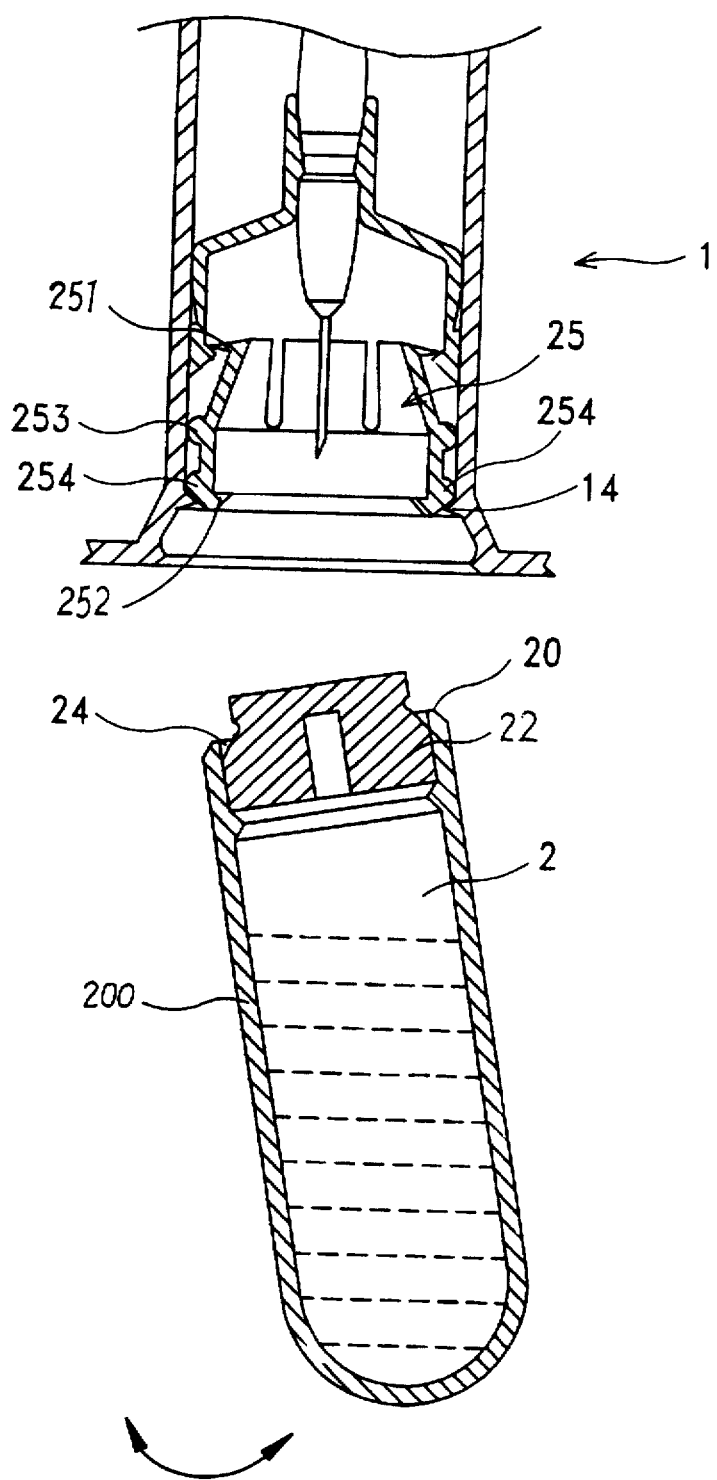
FIG. 4 is a schematic longitudinal sectional view of the preferred embodiment of the present invention when a vacuum container having blood therein is pulled out of the syringe.

Please refer to FIG. 4, as the vacuum container 2 is pulled to the end, the annular flange 254 will be stopped by the annular flange 14, and the neck 20 is exposed within the horn opening 18 and can be bended to break, thus the vacuum container 2 can be removed off with the snapping member 25 remained within the barrel 1.

Figure 6:
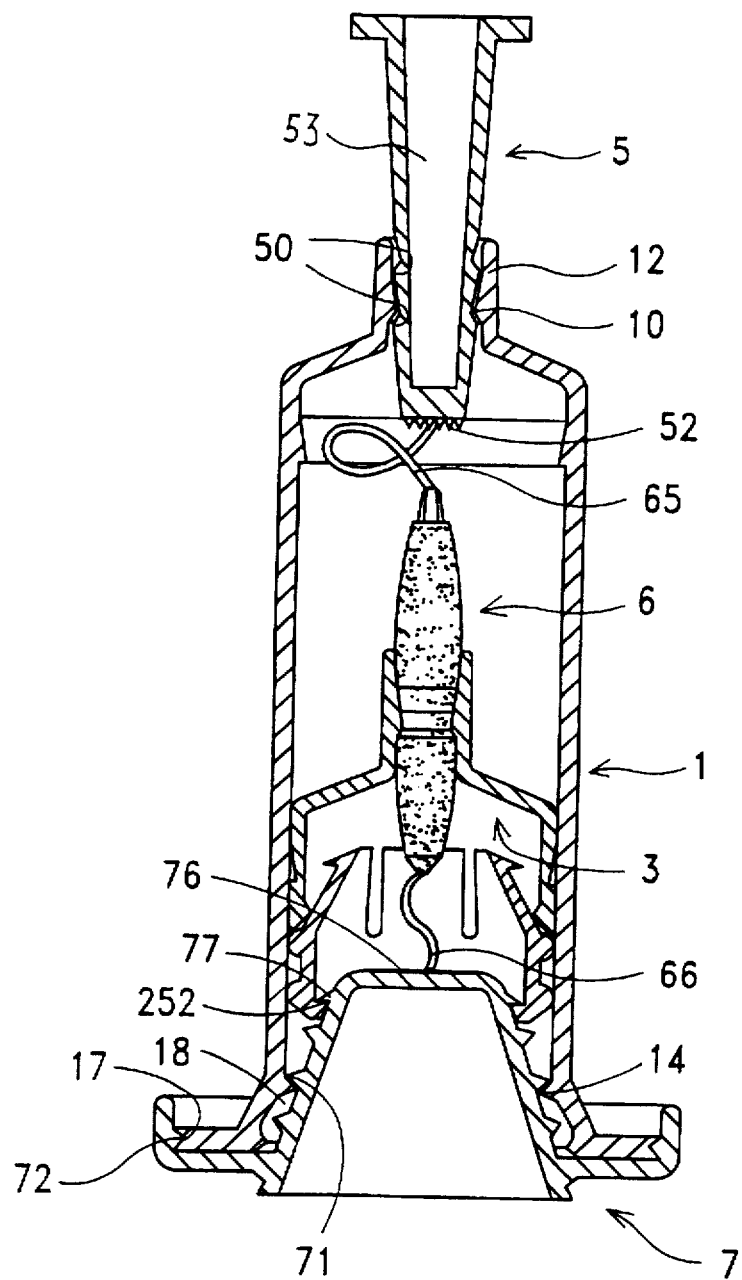
FIG. 6 is a schematic longitudinal sectional view of the preferred embodiment of the present invention when a needle cap and a bottom cap are reversely inserted into the barrel of the syringe so that the two opposite needles are bent to be damaged.

Please refer to FIG. 6, which shows that the needle cap 5 and the bottom cap 7 are reversely inserted into the contracted opening 12 and the horn opening 18 respectively after the vacuum container 2 is removed off. The annular hook recess 50 will be snapped with the slope annular flange 10, and the the annular flange 71 will be snapped with the annular flange 14, while the annular hook flange 77 will be hooked with the annular hook flange 252. Since the distance between the closed end 52 and the bottom surface 76 can be pushed to be less than the total length of the needle unit 6, the front needle 65 and the back needle 66 will be bent to be damaged, the syringe can therefore be discarded safely without hurting anybody.

Please refer to FIG. 7 and 8, which show another embodiment of the present invention that can be adapted to a syringe with thicker needles. Since a thicker needle is not easy to be bent, the needle cap 5 and bottom cap 7 are modified that the needle cap 5 is extended further to form a tube 56 having a tube opening 54 at the top end for accommodating the front needle 65 when revesely inserted into the barrel 1 as shown in FIG. 8, and similarly the bottom cap 7 will be provided with a recessed part 75 at bottom surface 76 thereof, when the bottom cap is reversely inserted into the barrel 1, the back needle 66 can be accommodated within the recessed part 75 as shown in FIG. 8.

The above embodiments can be modified by any skillful person in the art without departing the spirit and scope of the accompanying claims.

What is claimed is:

1. A safety vacuum syringe with two opposite needles for blood sampling, comprising;

a cylindrical barrel having a contracted opening at front end thereof and a horning opening at back end thereof.

a bell type sleeve having a bell body and a contracted tube at front end thereof for being inserted into said contracted opening of said barrel and fixed by means of a slope annular flange on said barrel, an annular hook flange being provided inwardly at a bottom opening of said bell body;

a needle unit having a needle rod extended through a rubber holder to form a front needle and a back needle, and having a slope annular recess at a waist part of said rubber holder for matching with a slope annular flange in said contracted tube;

a cylindrical vacuum container having a plasic tube and a rubber stopper for sealing said plastic tube, and having a snapping member connected with said plastic tube by a neck, an annular hook flange extended outwardly being provided at front end of said snapping member, a plurality of longitudinal slots provided at upper half wall of said snapping member to form a plurality of flexible snapping pieces, an annular hook flange provided inwardly at bottom end of said snapping member, and a plurality of annular flanges provided at outer circumference of said snapping member;

a needle cap having a front closed end and a back opening flange extended outwardly, and tapered from said flange toward said closed end for being able to just cover said rubber holder; and a bottom cap provided to be adapted to said horn opening of said barrel, having an annular flange provided at opening of said bottom cap and extended downward to form an annular wall, another annular flange provided inside of said annular wall, an annular recess provided at top edge of said bottom cap;

when it is desired to sample blood, said vacuum container is pushed into said barrel through back end thereof so that said plurality of flexible snapping pieces of said snapping member are pushed into said bell body, when finished of a blood sampling, said vacuum container is pulled backward so that said annular hook flange of said snapping member is hooked with said annular hook flange of said bell body to pull said bell type sleeve and said needle unit back into said barrel, and said needle cap and said bottom cap are then reversely inserted into said contracted opening and said horn opening respectively after said vacuum container is removed off by bending said neck to break, so that said front needle and said back needle can be bent to be damaged by said caps, and said syringe can therefore be discarded safely as a whole unit without hurting anybody.

2. The safety vacuum syringe with two opposite needles for blood sampling according to claim 1, wherein a top surface of said needle cap is made of a soft plastics.

3. The safety vacuum syringe with two opposite needles for blood sampling according to claim 1, wherein a top surface of said needle cap is made into a sawtooth shape.

4. The safety vacuum syringe with two opposite needles for blood sampling according to claim 1, wherein a top surface of said needle cap is made into a recessed shape.

5. The safety vacuum syringe with two opposite needles for blood sampling according to claim 1, wherein said needle cap is extended further to form a tube having a tube opening at top end thereof for accommodating said front needle when said needle cap is revesely inserted into said barrel.

6. The safety vacuum syringe with two opposite needles for blood sampling according to claim 1, wherein said bottom cap is provided with a recessed part at bottom surface thereof, when said bottom cap is reversely inserted into said barrel 1, said back needle can be accommodated within said recessed part.

* * * * *